US010022556B1

(12) United States Patent
Holbert et al.

(10) Patent No.: US 10,022,556 B1
(45) Date of Patent: Jul. 17, 2018

(54) COMPUTER CONTROLLED SOLID STATE LIGHTING ASSEMBLY TO EMULATE DIURNAL CYCLE AND IMPROVE CIRCADIAN RHYTHM CONTROL

(71) Applicant: United States of America as Represented by the Administrator of the National Aeronautics and Space Administration, Washington, DC (US)

(72) Inventors: Eirik Holbert, Cocoa, FL (US); Adam G. Dokos, Titusville, FL (US); Kelly J. Gattuso, Merritt Island, FL (US); Tracy R. Gill, Orlando, FL (US)

(73) Assignee: The United States of America as Represented by the Administrator of NASA, Washington, DC (US)

(*) Notice: Subject to any disclaimer, the term of this patent is extended or adjusted under 35 U.S.C. 154(b) by 7 days.

(21) Appl. No.: 14/750,641

(22) Filed: Jun. 25, 2015

Related U.S. Application Data (60) Provisional application No. 62/018,105, filed on Jun. 27, 2014.

(51) Int. Cl.
| | |
|---|---|
| *A61N 5/06* | (2006.01) |
| *H05B 33/08* | (2006.01) |
| *A61M 21/02* | (2006.01) |
| *A61M 21/00* | (2006.01) |

(52) U.S. Cl.
CPC ............ *A61N 5/0618* (2013.01); *A61M 21/02* (2013.01); *H05B 33/0815* (2013.01); *H05B 33/0857* (2013.01); *A61M 2021/0044* (2013.01); *A61N 2005/0626* (2013.01); *A61N 2005/0652* (2013.01); *A61N 2005/0663* (2013.01)

(58) Field of Classification Search
CPC .................. A61N 5/0618; A61N 21/02; A61N 2005/0626; A61N 205/0652; A61N 2005/0663; H05B 33/0815; H05B 33/857; A61M 2021/0044
See application file for complete search history.

(56) References Cited

U.S. PATENT DOCUMENTS

| | | | | |
|---|---|---|---|---|
| 7,598,686 | B2 * | 10/2009 | Lys | .................... H05B 33/0815 315/292 |
| 8,841,864 | B2 | 9/2014 | Maxik et al. | |

* cited by examiner

*Primary Examiner* — Lindsey G Wehrheim
(74) *Attorney, Agent, or Firm* — Jonathan J. Leahy; Michelle L. Ford; Mark P. Dvorscak (57) ABSTRACT

A light system can simultaneously emulate more than one different diurnal cycle to individually improve circadian rhythm control for more than one observer by having each light fixture autonomously self-controlled. Each light fixture is mountable in respective locations to individually treat respective observers. Each light fixture includes one or more light elements mounted to a housing and are controllable to emit a selected light intensity at a selected light temperature. A micro controller is contained in the housing and includes memory containing instructions for one or more automatic diurnal cycle protocols. The micro controller is in communication with the memory and the one or more light elements to execute the instructions to configure the light fixture to vary the light intensity and the light temperature of the emitted light.

17 Claims, 8 Drawing Sheets

COMPUTER CONTROLLED SOLID STATE LIGHTING ASSEMBLY TO EMULATE DIURNAL CYCLE AND IMPROVE CIRCADIAN RHYTHM CONTROL

CROSS-REFERENCE TO RELATED APPLICATIONS

This application claims the benefit of priority under 35 U.S.C. § 119(e) to U.S. Provisional Application Ser. No. 62/018,105 filed Jun. 27, 2014, the contents of which are incorporated herein by reference in their entirety.

ORIGIN OF THE INVENTION

The invention described herein was made by employees of the United States Government and may be manufactured and used by or for the Government of the United States of America for governmental purposes without the payment of any royalties thereon or therefore.

BACKGROUND OF THE INVENTION

1. Technical Field

The present invention generally relates to testing apparatus and methods of creating customized and automated lighting that mimics natural daylight patterns, and more particularly to individually programmable light fixtures that can be used to treat conditions related to circadian rhythms.

2. Description of the Related Art

The lack of a true diurnal cycle of sunlight, encompassing the same range of color temperatures and intensities of sunlight experienced on Earth, is one of the potential causes of sleep disorders among astronaut crews. The production of melatonin, a hormone that helps regulate sleep cycles, can be inhibited by light, especially low temperature blue light. To help regulate sleep cycles and improve the quality of sleep for the crew, control of the melatonin production cycle through the use of light is crucial. Commercial light therapy devices exist that allow for exposure to specific wavelengths of light using polychromatic polarized light, lasers, light-emitting diodes, fluorescent lamps, dichroic lamps, or very bright, full-spectrum light, usually controlled with various devices. An example is described in U.S. Pat. No. 8,841,864 to Maxik et al., the contents of which are hereby incorporated by reference in its entirety.

BRIEF SUMMARY OF THE INVENTION

In one aspect, the present invention provides a light system to simultaneously emulate more than one different diurnal cycle to individually improve circadian rhythm control for more than one observer. In one or more embodiments, the light system includes more than one light fixture that are mountable in respective locations to treat respective observers. Each light fixture includes one or more light elements that are mounted to a respective housing. Each light fixture is self-controllable to emit a selected light intensity at a selected light temperature. In particular, a micro controller is contained in the housing and includes a memory that contains instructions for one or more automatic protocols. The micro controller is in communication with the memory and the one or more light elements to execute the instructions to vary light intensity and light temperature (color) of emitted light by the light elements in accordance with the automatic protocols. In an exemplary embodiment, the light intensity and the light temperature can be varied according to a selected automatic diurnal cycle protocol.

In another aspect, the present invention provides a light fixture to emulate a diurnal cycle and to improve circadian rhythm control. In one or more embodiments, the light fixture includes one or more light elements that are mounted to a housing. The light fixture is self-controllable to emit a selected light intensity at a selected light temperature. In particular, a micro controller is contained in the housing and includes a memory that contains instructions for one or more automatic protocols. The micro controller is in communication with the memory and the one or more light elements to execute the instructions configure the light fixture to vary the light intensity and the light temperature in accordance with the protocol. In an exemplary embodiment, the light intensity and the light temperature can be varied according to a selected automatic diurnal cycle protocol.

In an additional aspect, the present invention provides a method of simultaneously emulating more than one different diurnal cycle to individually improve circadian rhythm control for more than one observer. In one or more embodiments, the method includes a controller contained in a light fixture dynamically adjusting a level of light intensity and a level of light temperature of the light fixture over one or more simulated diurnal cycles. In particular the method includes the controller maintaining a relative time value within the simulated diurnal cycle. The method includes the controller accessing a selected automatic diurnal cycle protocol that contains an assigned light intensity setting and an assigned light temperature as a function of the relative time value. The method includes the controller controlling a respective intensity of more than one light element that each having a different light temperature to create a resulting combined light output at a continuously selectable light intensity within a range of light intensities and a continuously selectable light temperature within a range of light temperatures.

The above summary contains simplifications, generalizations, and omissions of detail and is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present invention are shown and described with respect to the figures presented herein, in which.

DETAILED DESCRIPTION OF THE INVENTION

The present invention provides an apparatus and operating system to autonomously control the color temperature and intensity of light to simulate a true diurnal cycle for regulating human sleep patterns. The present invention, known as the Computer Controlled Solid State Lighting Assembly to Emulate Diurnal Cycle and Improve Circadian Rhythm Control (hereinafter "Circadian Rhythm Lighting Assembly" or "CRLA"), was designed and built to help regulate the sleep cycles of astronauts working on the International Space Station (ISS) and during long-duration spaceflight. Currently, the ISS crew is losing efficiency 4 to 5 months into its tour of duty, and sleep complaints are common among astronauts.

The CRLA was designed and built specifically to improve upon the inherent problems with the available commercial lighting technologies used to treat sleep disorders. Most commercially available lighting systems do not have the ability to adjust for both color temperature and intensity. In addition, many of the existing systems designed for light therapy have either one setting or only have a limited number of pre-set color temperatures and intensities.

The present invention is a programmable solid state general illumination fixture with full intensity and color temperature control between 2800 K and 5500 K. This new and novel lighting assembly uses a micro controller with a power relay to adjust color temperature and perceived intensity to simulate a practical diurnal cycle. Color temperature is fully adjustable over the entire range of temperatures. Light intensity can vary from a low "night light" level (to minimize or eliminate any delays to the initiation of Rapid Eye Movement (REM) sleep amongst the users) to a daylight or work mode level that can be implemented to aid in concentration on normal work day tasks. Lighting intensity can be a change in the modulation of a lighting element. A manual mode has been added to override the automatic diurnal cycle in the event of an out of cycle work requirement. Blue light is added to assist with circadian rhythm adjustment should sleep cycles need to be adjusted. The micro controller takes the primary control of the lighting scheme rather than a master controller, making individualized therapies possible.

Figure 1:
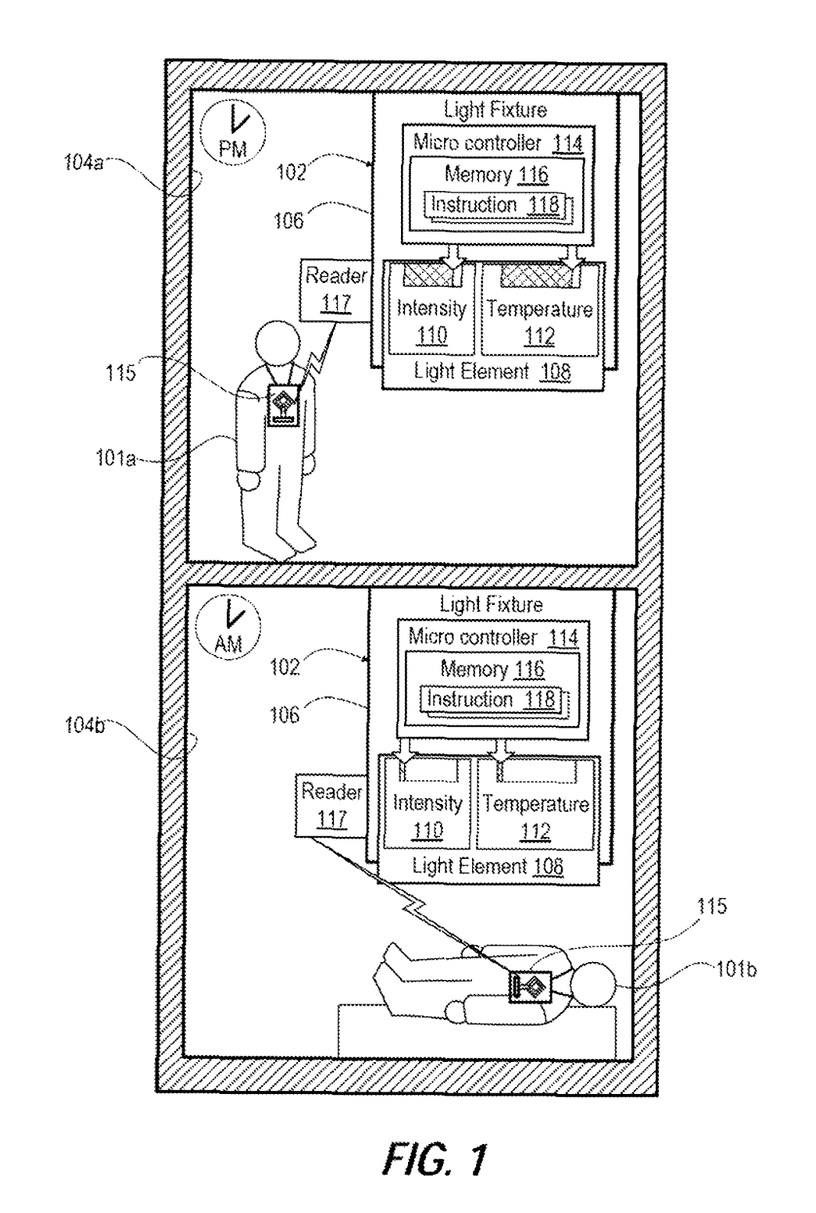
FIG. 1 illustrates a conceptual block diagram of a light system installed in a facility to simultaneously emulate more than one different diurnal cycle(s) to individually improve circadian rhythm control for more than one observer, according to one or more embodiments.

Turning to the Drawings, FIG. 1 illustrates a light system 100 to simultaneously emulate more than one different diurnal cycle to individually improve circadian rhythm control for more than one observer 101a, 101b. For example, the observers 101a, 101b can be on different work schedules and would benefit from individualized light therapy to maintain their sleep patterns. For another example, one observer 101a, 101b may be experiencing jet lag and can benefit from resetting his circadian rhythm through light therapy. In one or more embodiments, the light system 100 includes light fixtures 102 that are autonomously controlled and are mountable in respective locations 104a, 104b to individually treat respective observers 101a, 101b. Each light fixture 102 can include a housing 106 to which one or more light elements 108 are mounted. The light elements 108 are controllable to emit a selected light intensity 110 at a selected light temperature 112.

To that end, a micro controller 114 of each light fixture 102 is contained in the housing 106 and includes a memory 116 containing instructions 118 for one or more automatic diurnal cycle protocols. The micro controller 114 is in communication with the memory 116 and the one or more light elements 108 to execute instructions to vary the light intensity 110 and the light temperature 112 (color) according to a selected automatic diurnal cycle protocol.

Figure 2:
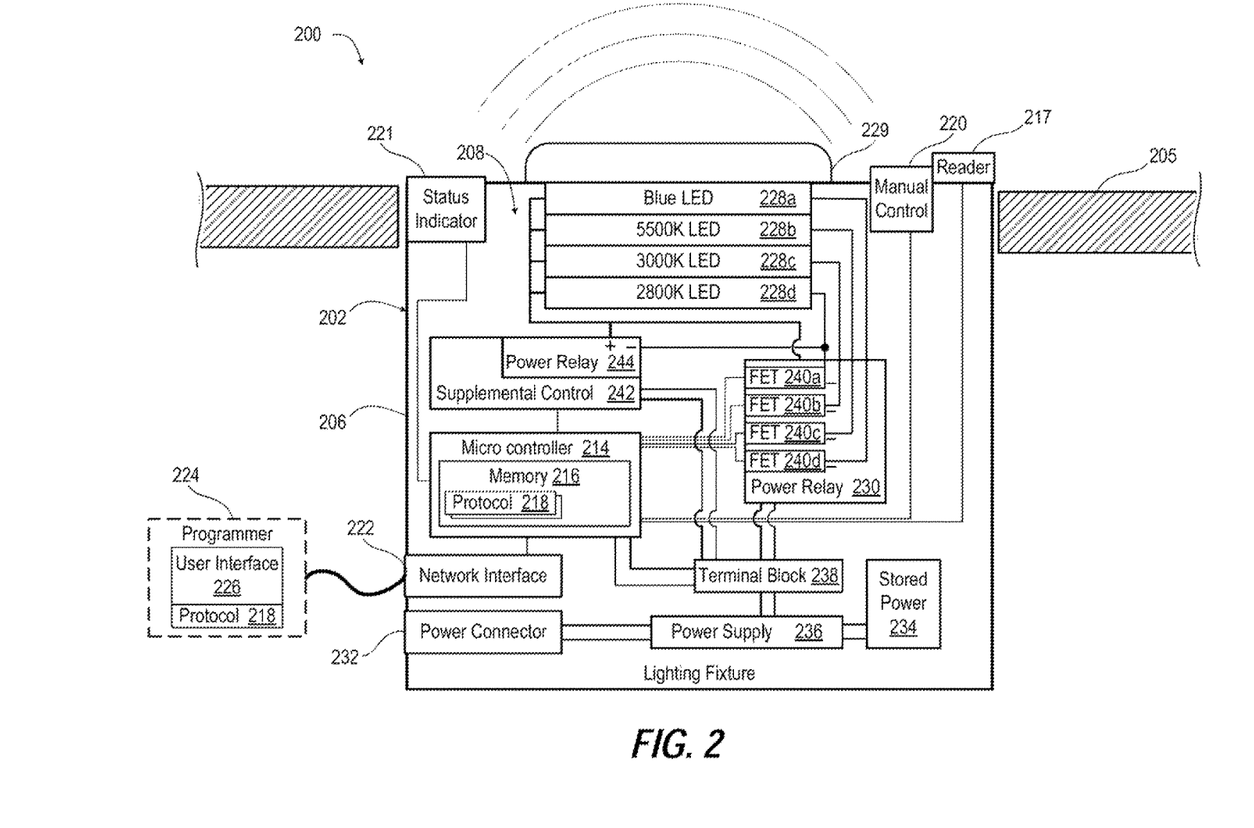
FIG. 2 illustrates a functional block diagram of an example light fixture of the light system of FIG. 1, according to one or more embodiments.

In one or more embodiments, the micro controller 114 is provisioned with selectable instructions or protocols that are executed according to an identity of an observer 101a, 101b. For example, the observer 101a, 101b can carry identifying indicia such as a Radio Frequency Identifier (RFID) card 115 that is interrogated by a reader 117 of the light fixture 102. Alternatively, the reader 117 can identify the observers 101a, 101b by a biometric characteristic such as facial recognition. Alternatively, the observer 101a, 101b can be identified not as an individual but as part of group that is assigned the same instructions or protocols, such as a member of the night shift. For example, the RFID card 115 can be encoded with information that informs the proximate light fixture 102 as to the subject time of day for the respective observer 101a, 101b. Each light fixture 102 can change light intensity and light color as an observer 101a, 101b enters the room. FIG. 2 illustrates a light system 200 including a light fixture 202 that is autonomously controlled from a mounting within a wall 205. The light fixture 202 can include a housing 206 to which one or more light elements 208 are mounted. The light elements 208 are controllable to emit a selected light intensity at a selected light temperature. To that end, a micro controller 214 is contained in the housing 206 and includes a memory 216 containing instructions in the form of protocols 218 for one or more automatic diurnal cycle protocols. The micro controller 214 is in communication with the memory 216 and the one or more light elements to vary the light intensity and the light temperature according to a selected automatic diurnal cycle protocol. The protocol can be selected based on an identity of an observer that is read by a reader 217.

A manual control 220 can be attached to the housing 206, such as a momentary switch activated by a push button. The micro controller 214 is in communication with the manual control 220 to receive a user input to select between a manual mode and the selected automatic diurnal cycle protocol. A status indicator 221 informs the observer as to the selected or current mode. A network interface 222 such as a Universal Serial Bus (USB) port can be attached to the housing 206. The memory 216 is in communication with the network interface 222 to receive and to store a selected automatic diurnal cycle protocol from a programmer 224. For example, a general purpose computer can provide a comprehensive user interface 226 for tailoring selected light temperatures in a continuous range between 2800 K and 5500 K and selected light intensities for an automatic diurnal cycle protocol 218 for a particular observer.

In one embodiment, the light elements 208 include more than one light emitting diode (LED) arrays, such as a 475 nm blue light LED array 228a, a 5500 K white light LED array 228b, and a 3000 K white light LED array 228c. In an exemplary embodiment, the light elements 208 further included a 2800 K LED array 228d for additional reduction in blue light. The light elements 208 can be under a diffuser lens 229. A power relay 230 provides power to the light elements 208. The power can be received from a power connector 232 or a stored power source 234 and regulated by a power supply 236 that is connected to the power relay 230 through a terminal block 238. The micro controller 214 can control the light elements 208 by Pulse Width Modulation (PWM) controlling respective field effect transistors (FETs) 240a-240d of the power relay 230. In one embodiment, the micro controller 214 controls the 2800 K LED array 228d via a supplemental control 242 having a power relay 244.

In an exemplary embodiment, the CRLA has four light circuits driven by power modulated field-effect transistors (FETs), which are in turn controlled by a micro controller. The four lighting circuits include a 2800 K white light LED circuit, a 3000 K white light LED circuit, a 5500 K white light LED circuit, and a 472 nm blue light LED circuit. The present invention utilizes three (3) color temperature white light balanced flexible LED strips with a micro controller and FET power relay to simulate a diurnal cycle. This gives the advantage of a more natural environment to those without access to physiologically "normal" day-night cycles. The programmability of the CRLA system allows the diurnal cycle to be custom tailored or reset, dependent on individual needs. Based on geriatric studies, personnel who are suffering from sleep disorders may be able to overcome the problem through a personalized program of light therapy. It will allow those who are suffering from sleepiness in the morning to have a different therapy from those who may be suffering during the afternoon or evening, or who are having trouble falling asleep or achieving a REM state. Using a micro controller eliminates the possibility of a master controller failure and minimizes the human error of mixing therapies. It also allows a gradual circadian rhythm shifting, if necessary. Similarly, this micro controller allows the light control to more closely account for the non-linear, logarithmic optical response to ambient lighting.

Programming can be performed through a dedicated Universal Serial Bus (USB) port with full control of both the automated diurnal mode and the manual modes. This programming can include individual specific adjustments to accommodate sleep irregularities such as sleep onset insomnia as well as early awakening insomnia. The programming is designed to maintain synchronization through simple pulse control, and they minimize desynchronization in the event of a lack of computer control without loss of ambient lighting. The lighting program takes into account activity schedules and is capable of augmenting the ability to shift work schedules through a fundamental adjustment in personal circadian rhythm.

Figure 3:
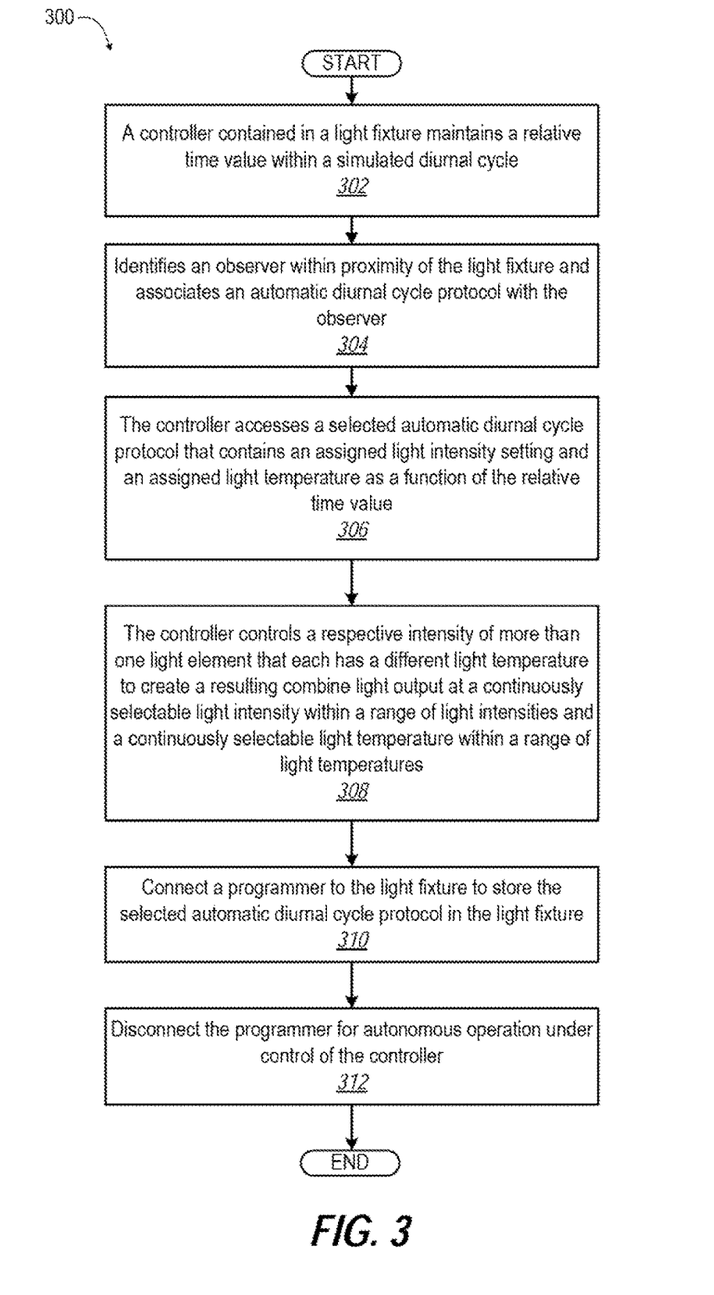
FIG. 3 illustrates a flow diagram of a method of autonomously controlling intensity and temperature color of a light fixture to emulate a diurnal cycle, according to one or more embodiments.

FIG. 3 illustrates a method 300 of simultaneously emulating more than one different diurnal cycle to individually improve circadian rhythm control for more than one observer. In one or more embodiments, the method 300 includes a controller contained in a light fixture maintaining a relative time value within the simulated diurnal cycle (block 302). The method 300 includes the controller identifying the observer within proximity of the light fixture and associating an automatic diurnal cycle protocol with the particular observer (block 304). The method 300 includes the controller accessing a selected automatic diurnal cycle protocol that contains an assigned light intensity setting and an assigned light temperature as a function of the relative time value (block 306). The method 300 includes the controller controlling a respective intensity of more than one light element that each has a different light temperature to create a resulting combined light output at a continuously selectable light intensity within a range of light intensities and a continuously selectable light temperature within a range of light temperatures. Thus, the controller dynamically adjusts a level of a light intensity and a level of a light temperature of the light fixture over one or more simulated diurnal cycles (block 308).

In one or more embodiments, the method 300 includes connecting a programmer to the light fixture to store the selected automatic diurnal cycle protocol in the light fixture (block 310). Then the method 300 includes disconnecting the programmer for autonomous operation under control of the controller (block 312).

In one or more embodiments, the method 300 includes the controller controlling the respective intensities of more than one light element which comprises pulse width modulating an FET that powers, respectively, each light element that comprises an LED array. For example, the one or more light elements can include two or more of a 3000 K white light LED, a 5500 K white light LED, a 475 nm blue light LED, and a 2800 K white light LED.

In one or more exemplary embodiments, the light system, light fixture, and method can work as follows: A software algorithm similar to an operating system running in the micro controller calculates the intensity of each of the light circuits. The micro controller converts that intensity into a PWM signal sent to the gate of the FET. Higher intensity corresponds to a larger duty cycle or a larger proportion of the time power is allowed to pass through the source and drain the FET. In an early embodiment, the PWM frequency is 400 Hz and, for relatively larger intensities, this frequency produces minimal flicker. In an exemplary embodiment, the PWM frequency is 2 kHz and can be higher, depending on capabilities of the micro controller. With the micro controller controlling the intensity through the FET, the voltage from the power supply passes through the LED circuits, to the FET, which modulates the connection to the ground, thereby controlling intensity. A momentary switch is used as an input device to send a pulse to the micro controller. These pulses cycle the micro controller through the preprogrammed manual modes as well as placing it back into the preprogrammed automatic mode. All manual modes are still controlled by PWM handled by the micro controller and FET. These manual modes can be changed in the micro controller programming. Currently, they include various settings: off, daylight white on, as well as various evening and night light settings. Current manual modes also include a circadian phase shifting mode. This mode could be included in the automatic programming cycle as well, if needed. Manual modes are limited to a discrete number of preprogrammed circuit intensities. Programming is accomplished through a USB interface. The operating system can be updated for long-term adjustments for therapy. For short-term changes to the light output, the USB is capable of supporting a point-and-click interface. The point-and-click interface allows continuous adjustment of all circuits for creating far more than just the limited manual modes. However, this can require interface to a computer instead of the simple push button/switch input device for manual modes.

Figure 4:
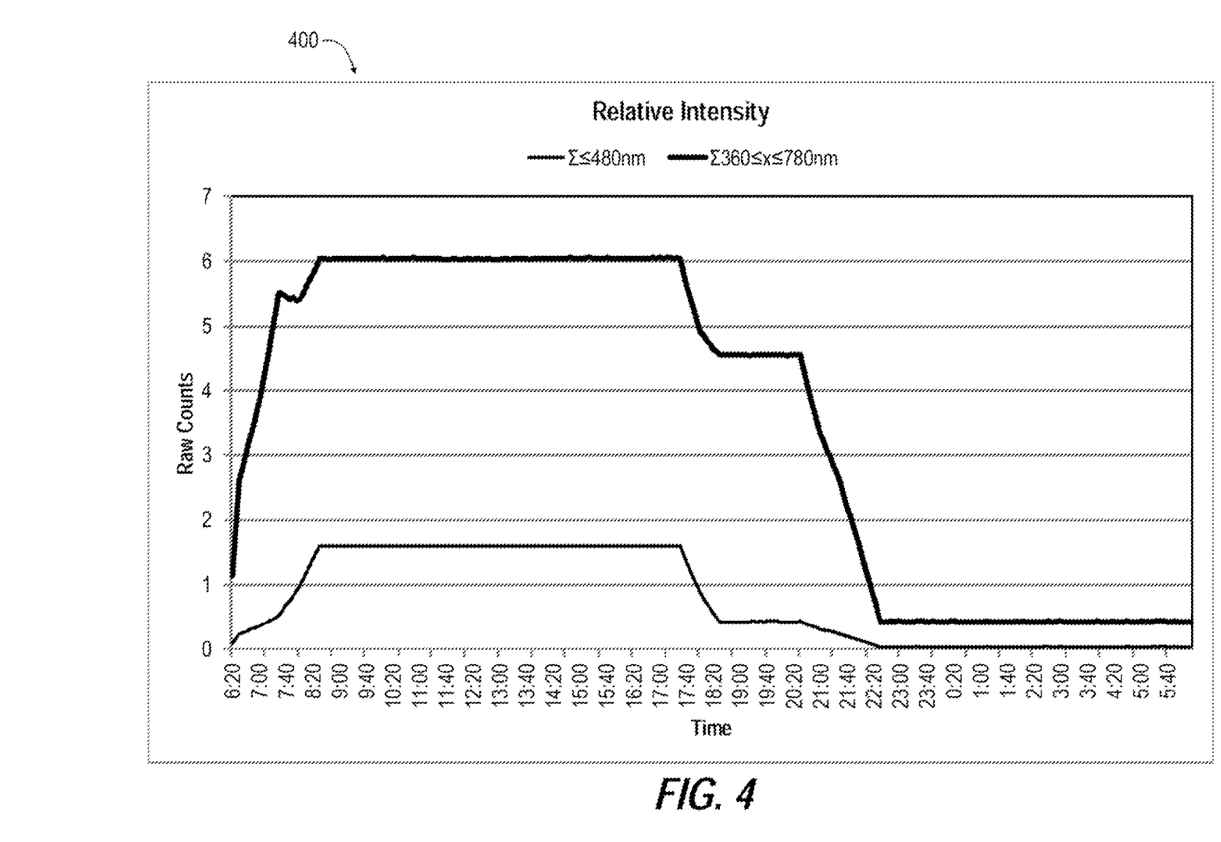
FIG. 4 illustrates a graphical plot of relative intensity, according to one or more embodiments.
Figure 5:
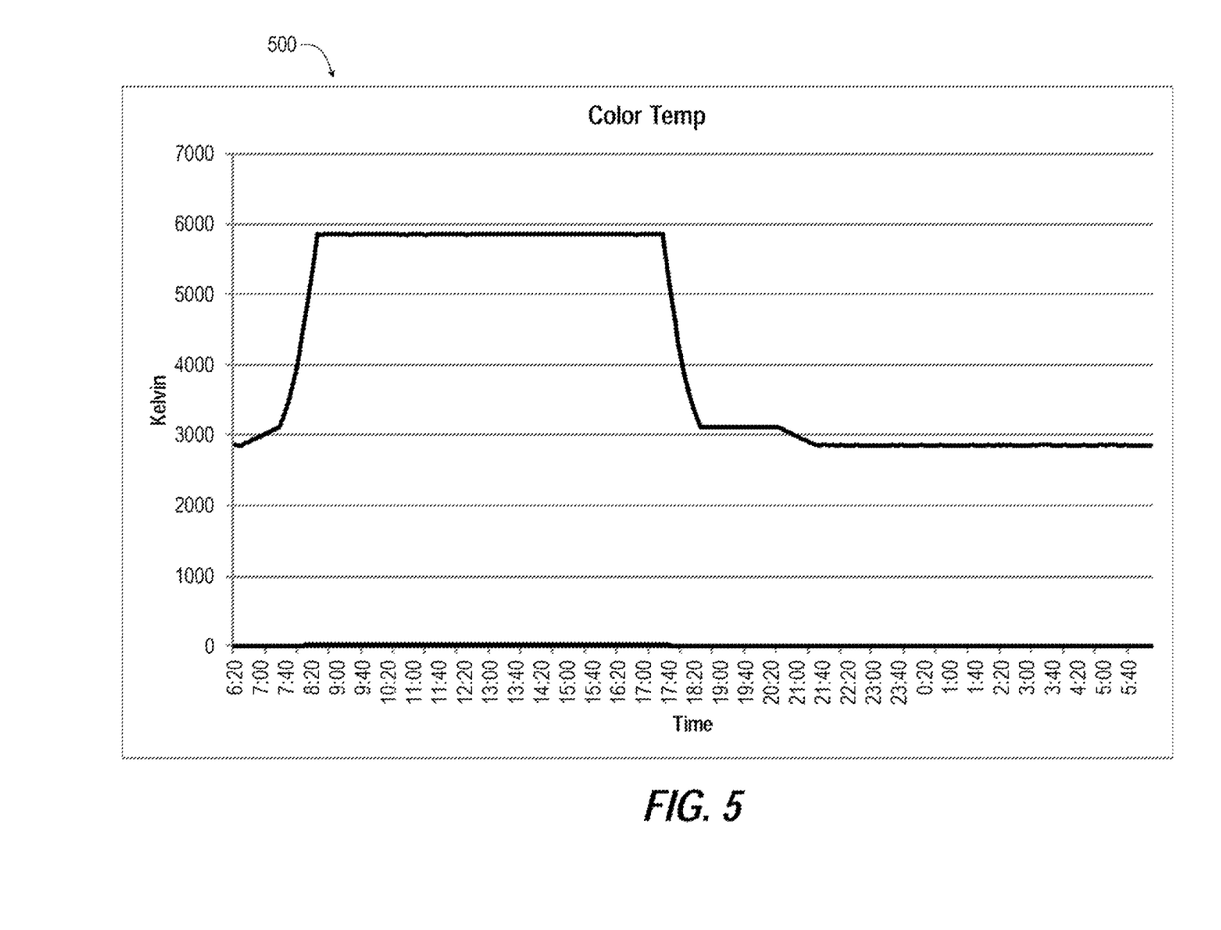
FIG. 5 illustrates a graphical plot of modulated color temperature, according to one or more embodiments.

Effectively, a "normal" work day under only this system's illumination would look something like the following: FIG. 4 illustrates a relative intensity plot 400. FIG. 5 illustrates a modulated color temperature plot 500.

Intensity gets brighter as you proceed to the beginning of the work day and the color temperature gets progressively higher (corresponding to a cooler color light) to mimic the diurnal cycle. As the work day ends, the light gets only slightly dimmer, but significantly lower in color temperature (i.e., the light gets warmer). As the sleep cycle begins, the components of the light become even less blue as the light intensity dims.

Again, this initial programming could be easily modified to adjust for any therapy required given the sleep situations of individual users. The diurnal cycle is not limited to 24 hours. It could easily be adapted to a 25-hour cycle, as some studies have shown this to be a more natural human cycle. At any time, this automatic programming could be interrupted through the direct computer interface, and the manual input mode can make any point on FIGS. 4 and 5.

The present invention was custom designed for the ISS to help regulate the sleep cycles of astronauts working on the ISS. However, the present invention can be implemented for use in other environments. Specifically, the invention can help treat sleep disorders on Earth such as Jet Lag; Shift Work Sleep Disorder (affects people who frequently rotate shifts or work at night); Delayed Sleep Phase Syndrome (the tendency to fall asleep very late at night, resulting in difficulty waking up in the morning for work or other engagements); Advance Sleep Phase Syndrome (the tendency to fall asleep very early in the evening and waking much earlier than desired, resulting in symptoms of evening sleepiness); and Non 24-Hour Sleep Wake Disorder (frequently affects those who are totally blind since the circadian clock is set by the light-dark cycle over a 24-hour period).

Figure 6:
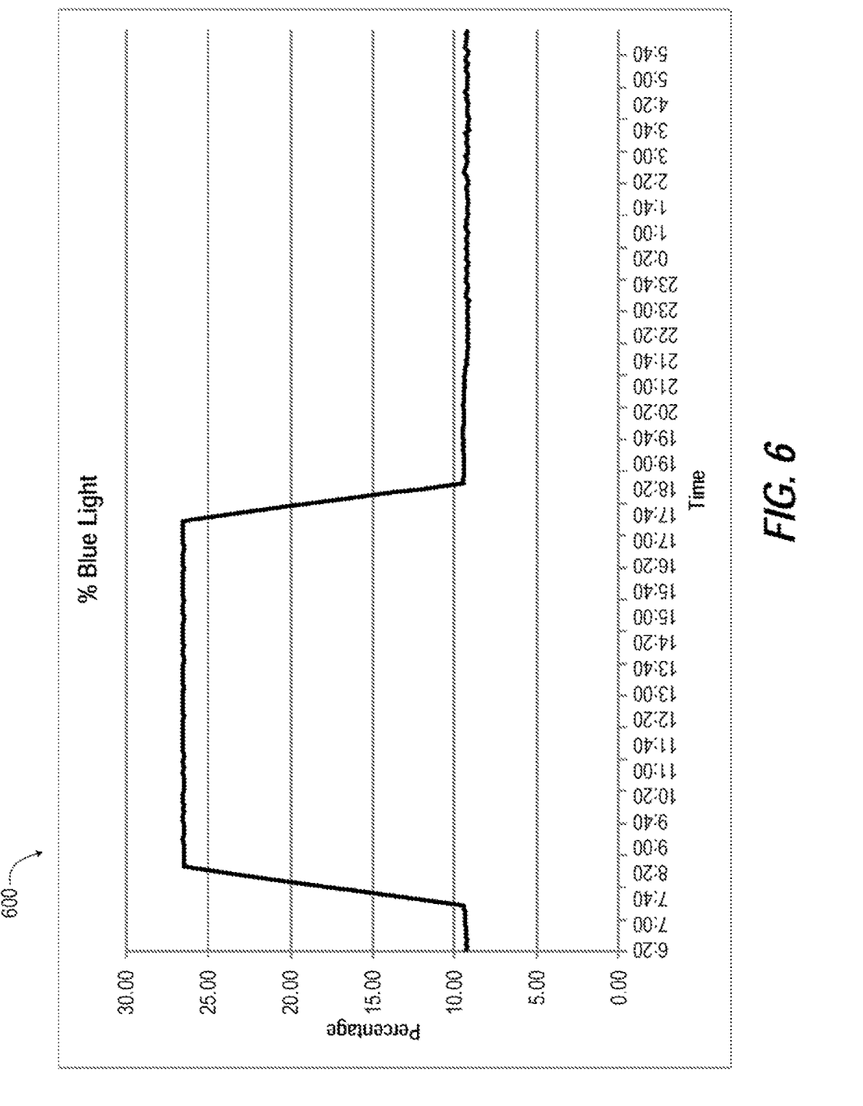
FIG. 6 illustrates a graphical plot of the percent of blue light over a diurnal cycle, according to one or more embodiments.

In addition, similar results could be achieved with three circuits, excluding the 2800 K circuit. White light LEDs use a blue exciting element to cause a specifically colored phosphor to fluoresce, simulating a white light of specific color temperature, dependent on the phosphor chosen. The 2800 K circuit emits approximately 3-4% less blue light than the 3000 K circuit. In an exemplary embodiment, FIG. 6 illustrates a plot 600 showing the percent of blue light over the diurnal cycle. Since the goal of the system is to minimize blue light exposure prior to sleep periods, the 2800 K circuit was used to minimize exposure to blue light during these times. However, it is possible to remove the 2800 K white light and achieve similar results.

Important considerations in designing a lighting fixture include costs of creation; flexibility in application, light outputs, beam distributions, and color; external fixture temperature; feasibility and ease of use, maintenance, powering, and repurposing; and optimal physical characteristics for its environment and use (e.g., weight, shape, size, portability, maneuverability). Further, although LEDs offer many benefits over other light sources, they are subject to light output depreciation over time, meaning that the ease at which individual LEDs can be changed is of crucial importance to maintaining targeted light levels. Moreover, given that the spectral composition of the light source is important for this particular application, it is important to dissipate heat to avoid wavelength shift. In terms of the fixtures functioning within a larger system, it is also important to consider the capacity of the chosen fixture to function independently (that is, have internal power and mode controls), as well as be manually overridden.

LED lighting systems offer tremendous advantages over traditional lighting fixtures in terms of reduced weight, increased durability and versatility, reduced energy use and ultraviolet radiation emission, and potential to be incorporated into a wide variety of designs. The present LED-based system will have direct applications for use in future space travel and scientific habitats.

In humans, light and dark patterns are the primary synchronizer of circadian rhythms to the 24-hour solar day. In the absence of a regular light-dark pattern, humans' circadian rhythms run with an average period of 24.2 hours. Daily light-dark patterns entrain circadian rhythms to the 24-hour solar day. Lack of entrainment leads to circadian disruption, which has been associated with a host of maladies. Humans not residing on the surface of the Earth, such as astronauts in the ISS, lack the 24-hour solar light and dark pattern provided by the Earth's rotation. The present invention seeks to provide a light and dark stimulus to regulate "healthy" circadian entrainment.

Experimental Data

In one exemplary embodiment (Example 1), the illumination area's dimensions are 3⅞×12 inches; and the fixture including casing has a surface dimension of 6⅝×26½ inches with a depth of 4 inches. The fixture consists of arrays of LEDs that can be combined to deliver various spectral irradiance combinations to obtain various correlated color temperatures (CCTs). The modes programmed in the fixture included CCTs of 2,800 K, 3,000 K, and 5,500 K, and a narrowband Blue LED.

The manual settings are noted in Table 1.

TABLE 1

Manual Setting for Example 1 Lighting Fixture

| | Source | | |
|---|---|---|---|
| | CCT | | Peale Wavelength |
| | Manufacturer | | |
| | 2700, 2750 or 2800K / 3000K | 5500 K or 6500K NASA msmts. | Blue |
| Setting | 2850K / 3100K | 5850K | 460-465 nm |
| Warm white (Evening) | 47 / 47 | 0 | 0 |
| Off | 0 / 0 | 0 | 0 |
| Dim warm white (night) | 10 / 0 | 0 | 0 |
| Cool white (day) | 0 / 0 | 100 | 0 |
| Phase shift | 0 / 0 | 50 | 50 |
| Blue | | | 100 |

Note:
Numbers are expressed in percentages per circuit so each row may or may not equal 100. Also, night runs the 2800K and 3000K at 120 of 255 pulse width modulation (PWM) steps for 47 percent.

The embodiment of Example 1 (the fixture) was evaluated to quantify the ability of the fixture as a source of circadian stimulus, based on photometric measurements and on calculations of circadian stimulus obtained using the model of human circadian phototransduction. More specifically, visual and circadian stimulation at varying distances were evaluated. Measures of visual stimulation (photopic light level) and circadian stimulation (ability to influence the circadian system as measured by acute melatonin suppression) were obtained at 1, 2, 3, and 4 feet from the fixture. See Table 2.

TABLE 2

Visual Stimulation (Light Level) and Circadian Stimulation Generated by Fixture, by Fixture Setting and Distance from Source *

| Fixture Setting | Visual Stimulation [Lux]** | | | | Circadian Stimulation *** | | | |
|---|---|---|---|---|---|---|---|---|
| | 1 foot | 2 feet | 3 feet | 4 feet | 1 foot | 2 feet | 3 feet | 4 feet |
| Warm white | 1440 | 409 | 187 | 107 | 0.561 | 0.350 | 0.208 | 0.130 |
| Dim warm white | 150 | 42.5 | 19.6 | 11.2 | 0.166 | 0.050 | 0.022 | 0.012 |
| Cool white | 1600 | 455 | 209 | 119 | 0.605 | 0.415 | 0.265 | 0.172 |
| Phase shift | 834 | 237 | 110 | 62.6 | 0.608 | 0.432 | 0.278 | 0.191 |
| Blue | 94.0 | 27.5 | 13.1 | 7.51 | 0.614 | 0.454 | 0.313 | 0.213 |

* Details on test methods provided below.
** Foveal task (e.g., reading black font on white paper); does not represent brightness perception.
*** Estimated percent melatonin suppression from 1-hour exposure, fixed pupil size of 2.3 mm.

To conduct the testing, the fixture of the present invention was furnished by NASA to the Lighting Research Center (LRC) at Rensselaer Polytechnic Institute. It is an array of LEDs housed behind a diffusing lens with the power supply and control circuit in a metal body. There is a single button to operate the fixture and a small yellow LED located near the button indicating the status of the fixture and the mode of operation. On the fixture, there are three ports for power and communication, a universal serial bus (USB) type-B female receptacle for programming the controller, an IEC 60320 C14 power inlet for powering the fixture on 120 Vac, and a 6 pin circular connector. Pressing the button once places the fixture in input mode, the indicator light flashes to confirm this. Repeatedly pressing the button cycles through the manual modes, shown by the indicator light being on, as well as the diurnal mode, shown by the indicator light being off. The manual mode continuously cycles through several conditions. The manual modes in which the fixture was measured were: warm white, dim warm white, cool white, phase shift (cool white and blue), and blue.

EVALUATION METRICS: Photometric data were collected to allow us to calculate the following metrics: photopic illuminance, chromaticity coordinates, correlated color temperature (CCT), circadian light ($CL_A$), circadian stimulus (CS), and luminous intensity distribution.

Photopic illuminance, measured in lux (lm/m2), is the luminous flux density measured on a surface (lm/area). Chromaticity is a measure of color characteristics as represented by x and y coordinates in the CIE 1931 color space. The CIE 1931 color spaces are the first defined quantitative links between physical pure colors (i.e. wavelengths) in the electromagnetic visible spectrum, and physiological perceived colors in human color vision. The mathematical relationships that define these color spaces are essential tools for color management. They allow one to translate different physical responses to visible radiation in color inks, illuminated displays, and recording devices such as digital cameras into a universal human color vision response. CIE 1931 RGB color space and CIE 1931 XYZ color space were created by the International Commission on Illumination (CIE) in 1931. The correlated color temperature (CCT) is a specification of the color appearance of the light ("warm" to "cool") emitted by a lamp, relating its color to that of a blackbody radiator at a particular temperature, measured in degrees Kelvin (K).

Circadian light ($CL_A$) is spectrally-weighted, effective irradiance at the cornea for stimulating the human circadian system (M. S. Rea et al. 2010). It is modeled from the combined response functions of four photoreceptors (rods, short-, middle-, and long-wavelength cones, and the intrinsically photosensitive retinal ganglion cells (ipRGCs)) to optical radiation and normalized so that a stimulus with a spectral power distribution (SPD) defined by CIE Illuminant A (a blackbody radiator at 2856 K, similar to an incandescent lamp) having a photopic illuminance at the cornea of 1000 lux equals a $CL_A$ of 1000. Only the model by Rea and colleagues provides estimates of both the spectral and absolute sensitivities of the circadian system. $CL_A$ is used to quantify the light stimulus before other physiological variables (e.g., pupil size, photoreceptor saturation) are taken into account for the absolute response of the human circadian system described by circadian stimulus (CS).

CS should be directly proportional to light-induced nocturnal melatonin suppression, from below threshold to above saturation, for 1-hour exposure during the middle of the subjective night for a standard observer. A fixed, 2.3 mm pupil diameter is assumed in the CS calculations. Thus, a calculated value of CS can be considered a predicted amount of nocturnal melatonin suppression resulting from a 1-hour exposure to a light stimulus of a given $CL_A$. CS can be derived from CL by using Equation 1. Values of CS range from 0 to 0.7, representing light-induced nocturnal melatonin suppression from 0% to 70%. Equation 1 represents Circadian Stimulus (CS) as a function of Circadian Light ($CL_A$):

$$CS = 0.75 - \frac{0.75}{1 + \left(\frac{CL_A}{215.75}\right)^{0.964}} \quad \text{Equation 1}$$

A luminous intensity distribution is the far-field spatial distribution of flux (lm/sr) generated by a source, in this case the fixture, and is reported in units of candela (cd). The term far-field refers to measurement distances being sufficiently far from the luminaire so that the physical size of the luminaire is negligible (i.e., it is treated as a point source). Typically, distances greater than five times the longest light emitting fixture dimension are considered far-field for architectural lighting calculations.

PROCEDURE: With the exception of the luminous intensity distribution, all of the evaluation metrics can be derived from spectral irradiance as measured by the Instrument Systems CAS 120 Array Spectrometer. The fiber coupled input optics of the spectrometer were tripod mounted above the fixture approximately centered to the lens. Readings were taken from 1, 2, 3, and 4 foot (ft.) distances as measured from the prominence of the lens to the input plane of the spectrometer, with the input plane parallel to the lens surface. Readings were taken using a 30 ms integration time for the measurements at 1 and 2 feet, and the auto integration time setting was used for the measurements at 3 and 4 feet. Each reading averaged ten samples. Spectral irradiance was collected for each of the five manual modes at the specified distances.

TWO-AXIS IMAGING GONIOPHOTOMETER MEASUREMENT: The two-axis imaging goniophotometer generates a complete ray-tracing source model of a light source by imaging the source from many different angles. The fixture was mounted in the Radiant Zemax Near-Field Measurement System (NFMS), and imaged in both the warm white and phase shift modes. A far-field intensity distribution is then calculated from the processed ray data using the Radiant Zemax ProSource software.

Figure 7:
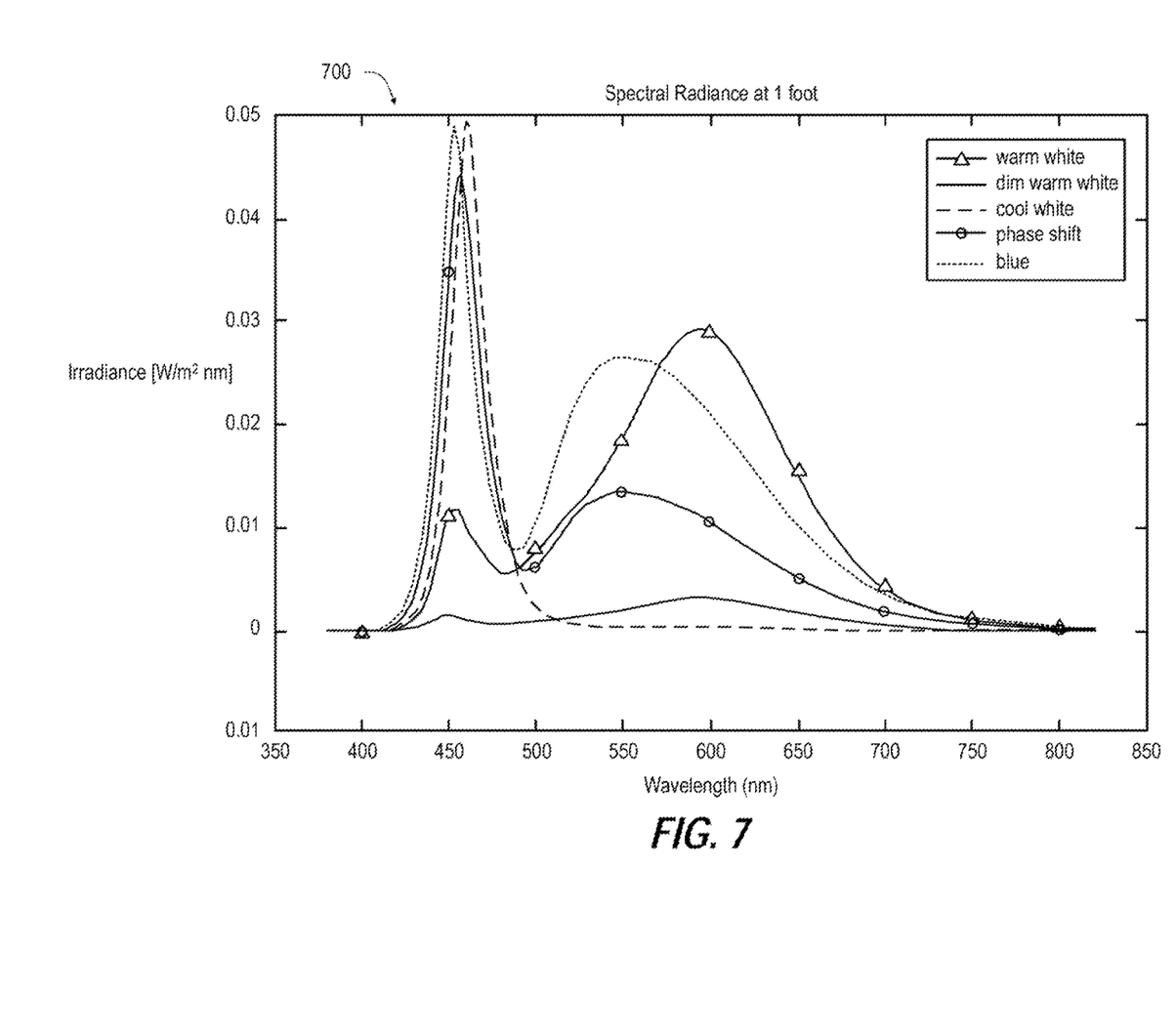
FIG. 7 illustrates a graphical plot of spectral irradiance from the fixture at 1 foot for characteristics of each manual mode, according to one or more embodiments.

SPECTRAL IRRADIANCE: FIG. 7 illustrates a plot 700 with the spectral irradiance from the fixture at 1 foot for characteristics of each manual mode. The cool white and blue modes peak at 452 nm and 460 nm, respectively, and combine to form the peak of the phase shift mode at 456 nm. Comparatively, the warm white mode has considerably less spectral irradiance below 500 nm and instead peaks around 600 nm. Spectral irradiances measured at 2, 3, and 4 feet have similar characteristics but overall less irradiance.

PHOTOPIC ILLUMINANCE: At all distances, the cool white mode had the highest illuminance with warm white the second highest. As one would expect, within the same mode, illuminance drops as distance from the fixture increases as supported by Table 3. This has important implications for consumer applications, given that one will not be sitting 1 foot away from the fixture; rather, it is more likely that a person and other objects illuminated by the fixture will be 3-4 feet away from the light.

TABLE 3

Photopic Illuminance [lux]

|  | 1 foot | 2 feet | 3 feet | 4 feet |
| --- | --- | --- | --- | --- |
| warm white | 1440 | 409 | 187 | 107 |
| dim warm white | 150 | 42.5 | 19.6 | 11.2 |
| cool white | 1600 | 455 | 209 | 119 |
| phase shift | 834 | 237 | 110 | 62.6 |
| blue | 94.0 | 27.5 | 13.1 | 7.51 |

CHROMATICITY: Chromaticity quantifies color based upon color matching functions for a standard observer. The chromaticity of any light or luminous object can be characterized by just two numbers (chromaticity coordinates), x and y. As can be seen from Table 4, there is little variation in the chromaticity of the sources with measured distance.

TABLE 4

CIE 1931 Chromaticity coordinates

|  | 1 foot | | 2 feet | | 3 feet | | 4 feet | |
| --- | --- | --- | --- | --- | --- | --- | --- | --- |
|  | x | y | x | y | x | y | x | y |
| warm white | 0.445 | 0.419 | 0.446 | 0.420 | 0.446 | 0.420 | 0.446 | 0.420 |
| dim warm white | 0.452 | 0.415 | 0.452 | 0.416 | 0.453 | 0.416 | 0.452 | 0.416 |
| cool white | 0.326 | 0.349 | 0.327 | 0.350 | 0.327 | 0.349 | 0.326 | 0.349 |
| phase shift | 0.279 | 0.273 | 0.278 | 0.272 | 0.277 | 0.270 | 0.277 | 0.269 |
| blue | 0.146 | 0.0583 | 0.145 | 0.0579 | 0.145 | 0.0579 | 0.145 | 0.0579 |

CORRELATED COLOR TEMPERATURE (CCT): The CCT rating for a "white" light source is intended to provide a general sense of its color appearance in terms of its "warmth" (low CCT) or "coolness" (high CCT). A CCT rating below 3200 K is usually considered "warm" and a CCT rating above 4000 K is usually considered "cool." The output of the blue mode does not have a CCT value because it is not "white." Table 5 provides CCT values for the different settings.

TABLE 5

Correlated Color Temperature (CCT) [K]

|  | 1 foot | 2 feet | 3 feet | 4 feet |
| --- | --- | --- | --- | --- |
| warm white | 2980 | 2980 | 2980 | 2980 |
| dim warm white | 2850 | 2850 | 2840 | 2840 |
| cool white | 5770 | 5740 | 5750 | 5760 |
| phase shift | 11200 | 11500 | 12000 | 12100 |
| blue | N/A | N/A | N/A | N/A |

Figure 8:
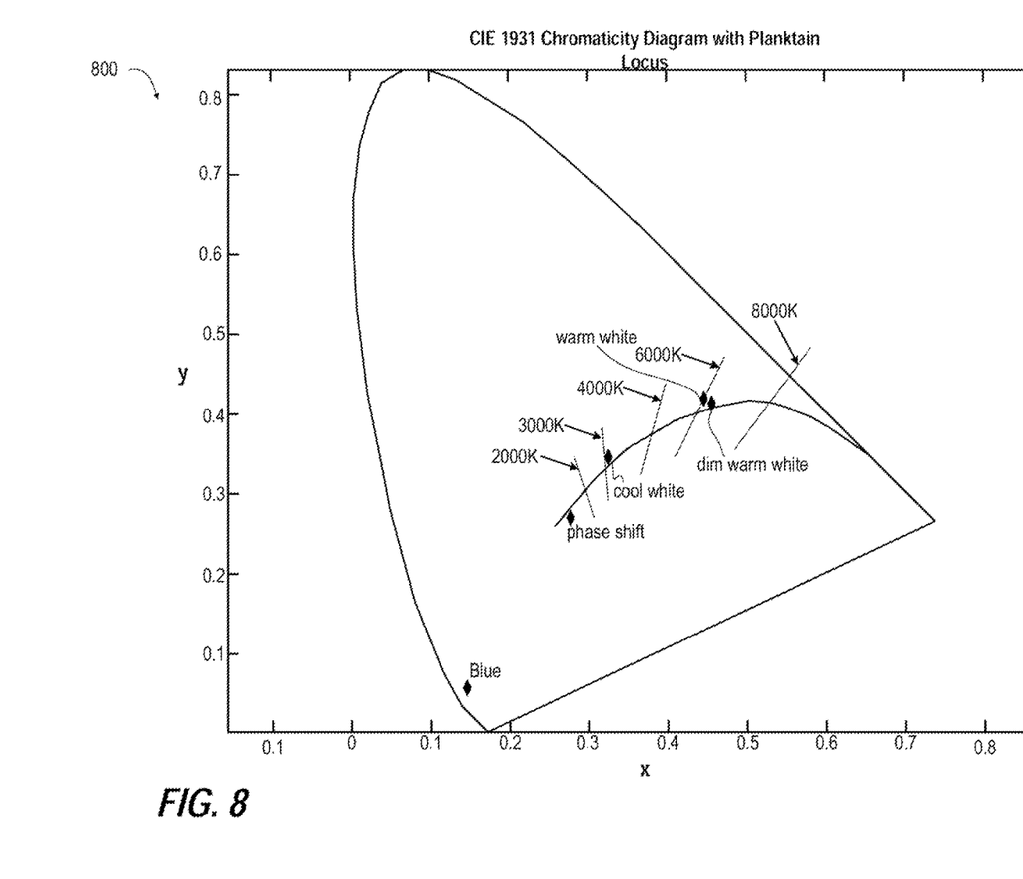
FIG. 8 illustrates a graphical plot of chromaticity of each operating mode in the CIE 1931 color space, according to one or more embodiments.

FIG. 8 illustrates a plot 800 of the chromaticity of each operating mode plotted in the CIE 1931 color space. The blackbody locus and several lines of constant CCT are also plotted for reference.

CIRCADIAN LIGHT ($CL_A$): Despite cool white having the highest illuminance, the blue mode produces the most $CL_A$ with the phase shift mode generating the second highest amount. This is consistent with the fact that the circadian system, as measured by acute melatonin suppression, is maximally sensitive to short-wavelength light. Warm white (both full and dim) produces the least amount of $CL_A$. This is expected since it lacks a strong short-wavelength component compared to the other modes. See Table 6. In fact, dim warm white has the lowest $CL_A$ primarily because of the much lower (over 10 times) irradiance.

TABLE 6

Circadian Light (CLA)

|  | 1 foot | 2 feet | 3 feet | 4 feet |
| --- | --- | --- | --- | --- |
| warm white | 1260 | 356 | 163 | 93.1 |
| dim warm white | 123 | 34.6 | 15.9 | 9.11 |
| cool white | 1920 | 501 | 227 | 129 |
| phase shift | 1970 | 549 | 256 | 146 |
| blue | 2120 | 619 | 294 | 168 |

CIRCADIAN STIMULUS (CS): As expected the CS shows the same rank ordering as $CL_A$ with the blue, phase shift, and cool white modes being the top three producers of CS and warm white and dim warm white the bottom two, as shown in Table 7. As mentioned above, dim warm white has the lowest CS not only because it has less emission at short wavelengths, but primarily because of the lower irradiance.

TABLE 7

Circadian Stimulus (CS)

|  | 1 foot | 2 feet | 3 feet | 4 feet |
| --- | --- | --- | --- | --- |
| warm white | 0.561 | 0.350 | 0.208 | 0.130 |
| dim warm white | 0.166 | 0.0499 | 0.0221 | 0.0121 |
| cool white | 0.605 | 0.415 | 0.265 | 0.172 |
| phase shift | 0.608 | 0.432 | 0.287 | 0.191 |
| blue | 0.614 | 0.454 | 0.313 | 0.213 |

SUMMARY OF EXPERIMENTAL RESULTS: Our calculations show that the narrowband short-wavelength light peaking close to the peak sensitivity of the circadian system is the most effective light source for stimulating the circadian system, even though it is not the one that provides the highest photopic illuminance. Two other important observations from our measurements are: 1) when it comes to the white light, changing spectrum from cool white to warm white will reduce CS for the same photopic illuminance, but this reduction will not be as significant as reducing irradiance, and 2) given that the absolute irradiances of the "white" light sources matter more than their spectrum, it is important to make measurements at meaningful distances from the source. For example, a short distance (1-2 feet from the fixture) may be relevant (or not) to astronauts in the space station, but this close distance is not likely to be what people experience in their own homes. It can be safely assumed that people will sit at least 3 feet from a fixture and will not be looking at it directly. More than one fixture can be used in a residential application to provide effective circadian stimulation.

In the following detailed description of exemplary embodiments of the invention, specific exemplary embodiments in which the invention may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present invention. It is also to be understood that other embodiments may be utilized and that logical, architectural, programmatic, mechanical, electrical, and other changes may be made without departing from the general scope of the invention. The following detailed description is, therefore, not to be taken in a limiting sense, and the scope of the present invention is defined by the appended claims and equivalents thereof.

References within the specification to "one embodiment," "an embodiment," "embodiments," or "one or more embodiments" are intended to indicate that a particular feature, structure, or characteristic described in connection with the embodiment is included in at least one embodiment of the present invention. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of a specific component, device, and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features, or concepts of the embodiments are provided solely as examples of one implementation, and such references do not limit the extension of the claimed embodiments to embodiments in which a different element, feature, protocol, or concept names are utilized. Thus, each term utilized herein is to be given its broadest interpretation given the context in which that terms is utilized.

While the invention has been described with reference to exemplary embodiments, it will be understood by those skilled in the art that various changes may be made and equivalents may be substituted for elements thereof without departing from the scope of the invention. In addition, many modifications may be made to adapt a particular system, device, or component thereof to the teachings of the invention without departing from the essential scope thereof. Therefore, it is intended that the invention not be limited to the particular embodiments disclosed for carrying out this invention, but that the invention will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope of the invention. The described embodiments were chosen and described in order to best explain the principles of the invention and the practical application, and to enable others of ordinary skill in the art to understand the invention for various embodiments with various modifications as are suited to the particular use contemplated.

We claim:

1. A light system to simultaneously emulate more than one different diurnal cycles to individually improve circadian rhythm control for more than one observer, the light system comprising:
    more than one light fixture mountable in respective locations to treat respective observers, each light fixture comprising:
    a housing;
    one or more light elements mounted to the housing and that are controllable to emit a selected light intensity at a selected light temperature;
    a micro controller contained in the housing and comprising a memory containing instructions for a light temperature and light color, the micro controller in communication with the memory and the one or more light elements to execute the instructions to vary a light temperature and light intensity of the emitted light; and
    wherein the one or more light elements of the more than one light fixture each comprise a light emitting diode (LED) array powered by a field effect transistor (FET) that is controlled for light intensity of the LED array by Pulse Width Modulation (PWM) by the micro controller, each LED array having a light temperature and a resulting light temperature from a combination of the LED arrays being continuously selectable across a range of light temperatures by assigning a respective portion of the light intensity to each LED array.

2. The light system of claim 1, wherein the micro controller executes the instructions to vary the light intensity and the light temperature according to a selected automatic diurnal cycle protocol.

3. The light system of claim 1, wherein each light fixture further comprises a manual control attached to the housing, wherein the micro controller is in communication with the manual control to receive a user input to select between a manual mode and the selected automatic protocols.

4. The light system of claim 1, wherein:
each light fixture further comprises a network interface attached to the housing, wherein the memory is in communication with the network interface to receive and store a selected automatic protocol; and
the light system further comprises a programmer to selectively communicate to the network interface of a selected light fixture to send the instructions.

5. The light system of claim 1, wherein the one or more light elements of each light fixture are controllable for selected light temperatures in a continuous range between 2800 K and 5500 K.

6. The light system of claim 1, wherein the one or more light elements comprise a 3000 K white light LED, a 5500 K white light LED, and a 475 nm blue light LED.

7. The light system of claim 6, wherein:
the one or more light elements of each light fixture comprises a blue light LED; and
the micro controller selectively activates the blue light LED to adjust a circadian rhythm of an observer.

8. The light system of claim 6, wherein the one or more light elements further comprise a 2800 K white light LED for minimizing blue light during a sleep period.

9. The light system of claim 1, wherein:
each light fixture further comprises a reader to identify an observer within proximity of the light fixture; and
the micro controller executes the instructions to associate the identity of the observer with a selected protocol for varying the light intensity and the light temperature.

10. A light fixture to emulate diurnal cycle and to improve circadian rhythm control, the light fixture comprising:
a housing;
one or more light elements mounted to the housing and are controllable to emit a selected light intensity at a selected light temperature;
a micro controller contained in the housing and comprising a memory containing instructions for one or more automatic protocols, the micro controller in communication with the memory and the one or more light elements to execute the instructions to configure the light fixture to vary a light intensity and a light temperature in accordance with the automatic protocol; and
wherein the one or more light elements each comprise a light emitting diode (LED) array powered by a field effect transistor (FET) that is controlled for light intensity of the LED array by Pulse Width Modulation (PWM) by the micro controller, each LED array having a light temperature and a resulting light temperature from a combination of the LED arrays being continuously selectable across a range of light temperatures by assigning a respective portion of the light intensity to each LED array.

11. The light fixture of claim 10, wherein the micro controller varies the light intensity and the light temperature of the emitted light according to a selected automatic diurnal cycle protocol.

12. The light fixture of claim 10, further comprising a manual control attached to the housing, wherein the micro controller is in communication with the manual control to receive a user input to select between a manual mode and the selected automatic protocol.

13. The light fixture of claim 10, further comprising a network interface attached to the housing, wherein the memory is in communication with the network interface to receive and to store a selected automatic protocol.

14. The light fixture of claim 10, wherein the one or more light elements comprise a 3000 K white light LED, a 5500 K white light LED, and a 475 nm blue light LED.

15. The light fixture of claim 14, wherein:
the one or more light elements of each light fixture comprises a blue light LED; and
the micro controller selectively activates the blue light LED to adjust a circadian rhythm of an observer.

16. The light fixture of claim 14, wherein the one or more light elements further comprise a 2800 K white light LED for minimizing blue light during a sleep period.

17. A light fixture to emulate diurnal cycle and to improve circadian rhythm control, the light fixture comprising:
a housing;
one or more light elements mounted to the housing and are controllable to emit a selected light intensity at a selected light temperature; and
a micro controller contained in the housing and comprising a memory containing instructions for one or more automatic protocols, the micro controller in communication with the memory and the one or more light elements to execute the instructions to configure the light fixture to vary a light intensity and a light temperature in accordance with the automatic protocol; and
further comprising a reader to identify an observer, wherein the micro controller associates the instructions associated with the light intensity and the light temperature with the identity of the observer.

* * * * *